US006929929B2

(12) United States Patent
Buchner

(10) Patent No.: US 6,929,929 B2
(45) Date of Patent: Aug. 16, 2005

(54) METHOD FOR THE EXPRESSION OF PROTEINS IN IN VITRO TRANSLATION SYSTEMS WITH COEXPRESSION OF FOLDING HELPER PROTEINS

(75) Inventor: Johannes Buchner, Ihrlerstein (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 33 days.

(21) Appl. No.: 10/133,534

(22) Filed: Apr. 26, 2002

(65) Prior Publication Data

US 2002/0192743 A1 Dec. 19, 2002

(30) Foreign Application Priority Data

Apr. 30, 2001 (DE) .......................................... 101 21 235

(51) Int. Cl.[7] .............................. C12P 21/06; C12N 5/06
(52) U.S. Cl. .................. 435/68.1; 435/69.1; 435/320.1; 435/325
(58) Field of Search ................................ 435/235.1, 25, 435/68.1, 69.1, 320.1, 325; 514/8, 12

(56) References Cited

U.S. PATENT DOCUMENTS

2001/0044146 A1 * 11/2001 Dees et al. .............. 435/235.1

FOREIGN PATENT DOCUMENTS

| EP | 0774512 A2 | 5/1997 |
|---|---|---|
| EP | 0885967 A2 | 12/1998 |
| EP | 1016724 A2 | 7/2000 |
| WO | WO 93/25681 | 12/1993 |
| WO | WO 94/24303 | 10/1994 |
| WO | WO 00/08135 | 2/2000 |

OTHER PUBLICATIONS

Abravaya, Klara et al., "The human heat shock protein hsp70 interacts with HSF, the transcription factor that regulates heat shock gene expression," Genes & Development 6:1153–1164, 1992.

Amrein, Kurt E. et al., "Purification and characterization of recombinant human p50csk protein–tyrosine kinase from an *Escherichia coli* expression system overproducing the bacterial chaperones GroES and GroEL," Proc. Natl. Acad. Sci. USA, vol. 92, pp. 1048–1052, Feb. 1995, Biochemistry.

Arrigo, Andre–Patrick et al., "Dynamic Changes in the Structure and Intracellular Locale of the Mammalian Low–Molecular–Weight Heat Shock Protein," Molecular and Cellular Biology, Dec. 1988, p. 5059–5071, vol. 8, No. 12.

Baranov, Vladimir I. et al., "Gene Expression in Cell–Free System on Preparative Scale," Methods in Enzymology, vol. 217, pp. 123–142.

Beckmann, Richard P. et al., "Interaction of Hsp 70 with Newly Synthesized Proteins: Implications for Protein Folding and Assembly," Science, vol. 248, May 18, 1990, pp. 850–854.

Beissinger, Martina et al., "How Chaperones Fold Proteins," Biol. Chem., vol. 379, pp. 245–259, Mar. 1998.

Bergman, Lawrence W. et al., "Formation of Intermolecular Disulfide Bonds on Nascent Immunoglobulin Polypeptides," The Journal of Biological Chemistry, vol. 254, No. 13, Issue of July 10, 1979, pp. 5690–5694.

(Continued)

Primary Examiner—Jon Weber
Assistant Examiner—Robert B. Mondesi
(74) Attorney, Agent, or Firm—Marilyn Amick; Roche Diagnostics Operations Inc.

(57) ABSTRACT

The present invention concerns a method for the expression of target proteins in in vitro translation systems, characterized in that folding helper proteins are co-expressed in this system. The co-expressed folding helper proteins are selected from one or several of the following protein classes: Hsp70, Hsp60, Hsp90, Hsp100 protein family, the family of small heat shock proteins and isomerases.

18 Claims, 2 Drawing Sheets

OTHER PUBLICATIONS

Figure 1:
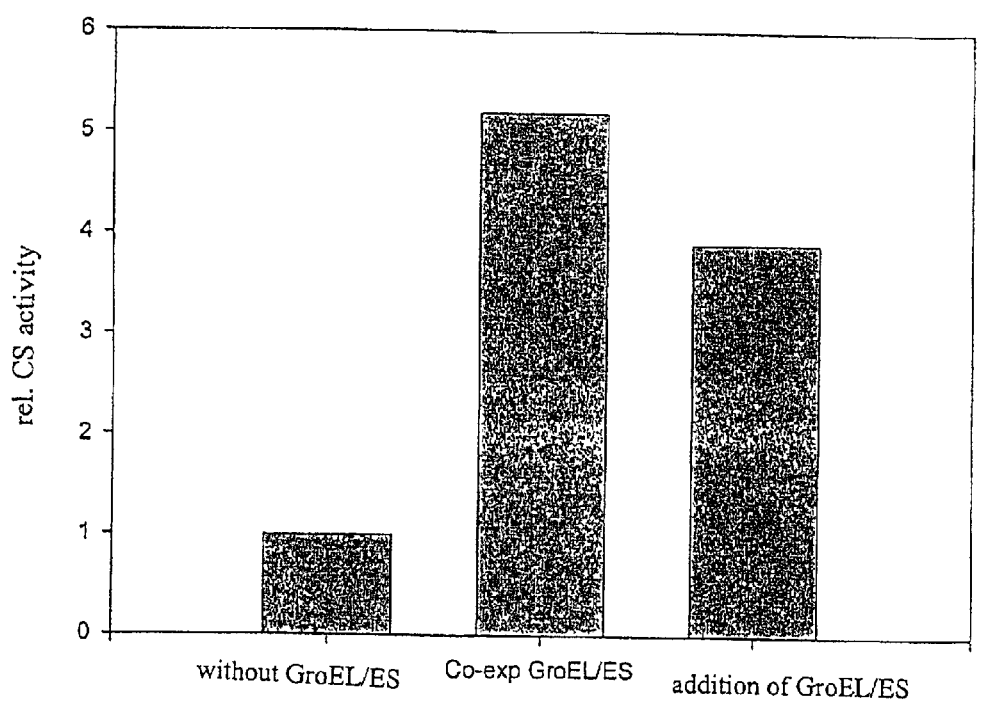

Bohen, Sean P. et al., "Hold 'em and Fold 'em: Chaperones and Signal Transduction," Science, vol. 268(5215), Jun. 2, 1995, pp. 1303–1304.

Braakman, Ineke et al., "Folding of Influenza Hemagglutinin in the Endoplasmic Reticulum," the Journal of Cell Biology, vol. 114, No. 3, Aug. 1991, 401–411.

Buchner, Johannes, "Hsp90 & Co.—a holding for folding," TIBS 24—Apr. 1999, pp. 136–141.

Buchner, Johannes et al., "Supervising the fold: functional principles of molecular chaperones," The FASEB Journal, vol. 10, Jan. 1996, 10–19.

Bukau, Bernd et al., "The Hsp70 and Hsp60 Chaperone Machines," Cell, vol. 92, 351–366, Feb. 6, 1998.

Chen, Hul–Zhu et al., "Prokaryotic Coupled Transcription–Translation," Methods in Enzymology, vol. 101, pp. 674–691, 1983.

Craig, Elizabeth A., "The Heat–shock Response of *Saccharomyces cerevisiae*," The Molecular and Cellular Biology of the Yeast Saccharomyces: Gene Expression, vol. II, pp. 501–537, 1992.

Dale, Glenn E. et al., "Increased solubility of trimethoprim-resistant type S1 DHFR from *Staphylococcus aureus* in *Escherichia coli* cells overproducing the chaperonins GroEL and GroES," Protein Engineering, vol. 7, No. 7, pp. 925–931, 1994.

Dekker, Peter J.T. et al., "The Role of Molecular Chaperones in Transport and Folding of Mitochondrial Proteins," 235–262, Institut fur Biochemic und Molekularbiologie, Universitat Freiburg, Hermann–Herder–St. 7, D–79140 Freiburg, Germany.

Eggers, Daryl K. et al., "Complexes between Nascent Polypeptides and Their Molecular Chaperones in the Cytosol of Mammalian Cells," Molecular Biology of the Cell, vol. 8, 1559–1573, Aug. 1997.

Ehrnsperger, Monika et al., "Binding of non–native protein to Hsp25 during heat shock creates a reservoir of folding intermediates for reactivation," The EMBO Jounal, vol. 16, No. 2, pp. 221–229, 1997.

Ehrnsperger, Monika et al., "Stabilization of Proteins and Peptides in Diagnostic Immunological Assays by the Molecular Chaperone Hsp251," Analytical Biochemistry 259, 218–225, 1998, Article No. AB982630.

Ewalt, Karla L. et al., "In Vivo Observation of Polypeptide Flux through the Bacterial Chaperonin System," Cell, vol. 90, 491–500, Aug. 8, 1997.

Falk, Matthias M. et al., "Cell–free synthesis and assembly of connexins into functional gap junction membrane channels," The EMBO Journal, vol. 16, No. 10, pp. 2703–2716, 1997.

Fenton, Wayne A. et al., "Residues in chaperonin GroEL required for polypeptide binding and release," Nature, vol. 371, Oct. 13, 1994, 614–618.

Fink, Anthony L. et al., "Chaperone–Mediated Protein Folding," Physiological Review, vol. 90, No. 2, Apr. 1999, pp. 426–449.

Frydman, Judith et al., "Folding of nascent polypeptide chains in a high molecular mass assembly with molecular chaperones," Nature, vol. 370, Jul. 14, 1994, pp. 111–117.

Ganea, Elena et al., "Molecular chaperones protect against glycation–induced inactivation of glucose–6–phosphated dehydrogenase," Eur. J. Biochem. 231, 181–185 (1995).

Georgopoulos, C. et al., "Role of the Major Heat Shock Proteins as Molecular Chaperones," Ann. Rev. Cell Biol., 1993, 9:601–34.

Gething, Mary–Jane et al., "Protein folding in the cell," Nature, vol. 355, Jan. 2, 1992, 33–45.

Goloubinoff, Pierre et al., "GroE heat–shock proteins promote assembly of foreign prokaryotic ribulose bisphosphate carboxylase oligomers in *Escherichia coli*," Nature, vol. 337, Jan. 5, 1989, 44–47.

Goloubinoff, Pierre et al., "Sequential mechanism of solubilization and refolding of stable protein aggregates by a bichaperone network," PNAS, Nov. 23, 1999, vol. 96, No. 24, pp. 13732–13737.

Gottesman, Susan, et al., "Regulatory Subunits of Energy–Dependent Proteases," Cell, vol. 91, 435–438, Nov. 14, 1997.

Gragerov, A.I. et al., "Protein aggregation and inclusion body formation in *Escherichia coli* rpoH mutant defective in heat shock protein induction," FEBS Letters 10270, vol. 291, No. 2, 222–224, Oct. 1991.

Gutsche, Irina et al., "Group II Chaperonins: New TriC(k)s and Turns of a Protein Folding Machine," J. Mol. Bio. (1999) 293, 295–312.

Hannavy, Kevin et al., "Protein import into mitochondria: a paradigm for the translocation of polypeptides across membranes," Current Opinion in Cell Biology, 1993, 5:694–700.

Hansen, William et al., "Complex Environment of Nascent Polypeptide Chains," The Journal of Biological Chemistry, vol. 269, No. 43, Issue of Oct. 28, pp. 26610–26613, 1994.

Hartl, F. Ulrich, "Molecular chaperones in cellular protein folding," Nature, vol. 381, Jun. 13, 1996, 571–580.

Haucke, Volker et al., "Reconstitution of the protein insertion machinery of the mitochondrial inner membrane," The EMBO Jounal, vol. 16, No. 15, pp. 4560–4567, 1997.

Hendrick, Joseph P. et al., "Molecular Chaperone Functions of Heat–Shock Proteins," Ann. Rev. Biochem., 1993, 62:349–84.

Horwitz, Joseph "α–Crystallin can function as a molecular chaperone," Proc. Natl. Acad. Sci. USA, vol. 89, pp. 10449–10453, Nov. 1992, Biochemistry.

Horwitz, Joseph et al., "Lensx–crystallin: function and structure," Eye (1999) 13, 403–408.

Huppa, Johannes B. et al., "In Vitro Translation and Assembly of a Compete T Cell Receptor–CD3 Complex," J. Exp. Med., vol. 186, No. 3, Aug. 4, 1997, 393–403.

Jaenicke, Rainer et al., "Folding proteins," Chapter 9, 191–223.

Jaenicke, Rainer et al., "Junior Chaperones," Current Biology 1993, vol. 3, No. 4, 234–235.

Jaenicke, Rainer, "Oligomeric Proteins," pp. 35–70, Molecular Chaperones in the Life Cycle of Proteins, Edited by Fink Al, Goto, Y., New York: Marcel Dekker 1998.

Jaenicke, Rainer et al., "Refolding and Association of Oligmeric Proteins," Methods in Enzymology, vol. 131, pp. 218–251.

Jakob, Ursula et al., "Assisting spontaneity: the role of Hsp90 and small Hsps as molecular chaperones," TIBS 19–May 1994, pp. 205–211.

Jakob, Ursula et al., "Small Heat Shock Proteins are Molecular Chaperones," The Journal of Biological Chemistry, vol. 268, No. 3, Issue of Jan. 25, pp. 1517–1520, 1993.

Jiang, XiuPing et al., "Expression of Fab fragment of catalytic antibody 6D9 in an *Escherichia coli* in vitro coupled transcription/translation system," FEBS Letters 514 (2002) 209–294.

Kiefhaber, Thomas et al., "Protein Aggregation In Vitro and In Vivo: A Quantitative Model of the Kinetic Competition Between Folding and Aggregation," Bio/Technology, vol. 9, Sep. 1991, 825–829.

Koehrer, Caroline et al., "Use of T7 RNA polymerase in an optimized Escherichia coli coupled in vitro transcription-translation system Application i regulatory studies and expression of long transcription units," Eur. J. Biochem., 236, 234–239 (1996).

Kruger, Elke et al., "Stress Induction of clpC in Bacillus subtillis and Its Involvement in Stress Tolerance," Journal of Bacteriology, Jun. 1994, vol. 176, No. 11, p. 3360–3367.

Lee, Garrett, J. et al., "A small heat shock protein stably binds heat–denatured model substrates and can maintain a substrate in a folding–competent state," The EMBO Journal, vol. 16, No. 3, pp. 659–671, 1997.

Lee, Garrett J. et al., "Structure and in Vitro Molecular Chaperone Activity of Cytosolic Small Heat Shock Proteins from Pea," The Journal of Biological Chemistry, vol. 270, No. 18, Issue of May 5, pp. 10432–10438, 1995.

Lillie, Hauke et al., "Influence of Protein Disulfide Isomerase (PDI) on Antibody Folding in Vitro," The Journal of Biological Chemistry, vol. 269, No. 19, Issue of May 13, pp. 14290–14296, 1994.

Liou, Anthony K. F. et al., "Elucidation of the subunit orientation in CCT (chaperonin containing TCPI) from the subunit composition of CCT mirco–complexexs," The EMBO Journal, vol. 16, No. 14, pp. 4311–4316, 1997.

Lorimer, George H. et al., "A quantitative assessment of the role of the chaperonin proteins in the protein folding in vivo," The FASEB Journal, vol. 10, Jan. 1996, pp. 5–9.

Matts, Robert L. et al., "The Relationship between Protein Synthesis and Heat Shock Proteins Levels in Rabbit Reticulocyte Lysates," The Journal of Biological Chemistry, vol. 267, No. 25,Issue of Sep. 5, pp. 18168–18174, 1992.

Matveev, S.V. et al., "Effect of the ATP level on the overall protein biosynthesis rate in a wheat germ cell–free system," Biochimica et Biophysica Acta 1293 (1996) 207–212.

Mosca, Joseph D. et al., "Restoration of Protein Synthesis in Lysed Rabbit Reticulocytes by the Enzymatic Removal of Adenosine 5'–Monophosphate with either AMP Deaminase or AMP Nucleosidase," Biochemistry, vol. 22, No. 2, 1983, pp. 346–353.

Pace, C. Nick et al., "How to determine the molar absorbance coefficient of a protein," 11: Optical spectroscopy to characterize protein conformation, pp. 253–297.

Parsell, Dawa A. et al., "Protein disaggregation mediated by heat–shock protein Hsp104," Nature, vol. 371, Dec. 1, 1994, 475–478.

Pelham, Hugh R. B. et al., "An Efficient mRNA–Dependent Translation System from Reticulocyte Lysates," Eur. J. Biochem., 67, 247–256 (1976).

Peters, Theodore Jr. et al., "The Biosynthesis of Rat Serum Albumin," The Journal of Biological Chemistry, vol. 257, No. 15, Issue of Aug. 10, pp. 8847–8853, 1982.

Ryabova, Lyubova A. et al., "Continuous–Flow Cell–Free Translation, Transcription–Translation, and Replication–Translation Systems," Methods in Molecular Biology, vol. 77: Protein Synthesis: Methods and Protocols, pp. 179–193.

Schatz, Gottfried et al., "Common Principles of Protein Translocation Across Membranes," Science, vol. 271, Mar. 15, 1996, pp. 1519–1526.

Schirmer, Eric C. et al., "An Arabidopsis Heat Shock Protein Complements a Thermotolerance Defect in Yeast," The Plant Cell, vol. 6, 1899–1909, Dec. 1994.

Schmidt, Marion et al., "Correlation between the Stability of the GroEl–Protein Ligand Complex and the Release Mechanism," The Journal of Biological Chemistry, vol. 269, No. 45, Issue of Nov. 11, pp. 27964–27972, 1994.

Sigler, Paul B. et al., "Structure and Function in GroEL–Mediated Protein Folding," Annu. Rev. Biochem. 1998, 67:581–608.

Spector, Abraham et al., "x–Crystallin," Biochem. J. (1971) 124, 337–343.

Spirin, Alexander S. et al., "Cell–Free Prtein Synthesis Bioreactor," American Chemical Society, pp. 31–43, 1992.

Spirin, Alexander S. et al., "A Continuous Cell–Free Translation System Capable of Producing Polypeptides in High Yield," Science, Nov. 25, 1998, 1162–1164.

Spirin, Alexander S., "Ribosome Preparation and Cell–Free Protein Synthesis," Chapter 2, Institute of Protein Research, Academy of Sciences of the USSR, Moscow Region, USSR, pp. 56–70.

Stiege, Wolfgang et al., "The potentials of the in vitro protein biosynthesis system," Journal of Biotechnology 41 (1995) 81–90.

Sullivan, William et al., "Nucleotides and Two Functional States of hsp90," The Journal of Biological Chemistry, vol. 272, No. 12, Issue of Mar. 21, pp. 8007–8012, 1997.

Tulin, Edgardo E. et al., "Continuously Coupled Transcription–Translation System for the Production of Rice Cytoplasmic Aldolase," Biotechnology and Bioengineering, vol. 45, pp. 511–516, 1995.

Tyedmers, Jens et al., "Assembly of heterodimeric luciferase after de novo synthesis of subunits in rabbit reticulocyte lysate involves hsc70 and Hsp40 at a post–tranlational stage," Eur. J. Biochem., 267, 3575–3582 (2000) FEBS 2000.

Vickery, Larry E. et al., "Hsc66 and Hsc20, a new heat shock cognate molecular chaperone system from Escherichia coli," Protein Science (1997), 6:1047–1056.

Weissman, Jonathan S. et al., "Efficient catalysis of disulphide bond rearrangements by protein disulphide isomerase," Nature, vol. 365, Sep. 9, 1993, pp. 185–188.

Welch, William J. et al., "Purification of the Major Mammalian Heat Shock Proteins," The Journal of Biological Chemistry, vol. 257, No. 24, Issue of Dec. 25, pp. 14949–14959, 1982.

Wunderlich, Martina et al., "Redox properties of protein disulfide isomerase (DabA) from Escherichia coli," Protein Science (1993), 2, 717–726.

Yao, Shui–Liang et al., "Biochemical Energy Consumption by Wheat Germ Extract during Cell–Free Protein Synthesis," Journal of Fermentation and Bioengineering, vol. 84, No. 1, 7–13, 1997.

Zubay, Geoffrey, "In Vitro Sysnthesis of Protein in Microbial Systems," Department of Biological Sciences , Columbia University, New York City, 3056, pp. 267–287.

"Expression of Recombinant Proteins," Chapter 1.4, Soluble recombinant proteins in E. Coli, XP–002135427, pp. 40–44.

* cited by examiner

METHOD FOR THE EXPRESSION OF PROTEINS IN IN VITRO TRANSLATION SYSTEMS WITH COEXPRESSION OF FOLDING HELPER PROTEINS

This application claims priority to German patent application 10121235.6 filed Apr. 30, 2001.

The present invention concerns a method for the expression of target proteins in in vitro translation systems, characterized in that folding helper proteins are co-expressed in this system. The co-expressed folding helper proteins are selected from one or several of the following protein classes: Hsp70-, Hsp60-, Hsp90-, Hsp100-protein family, the family of small heat shock proteins and isomerases.

The folding of large oligomeric proteins in vitro is frequently impaired by the occurrence of aggregation (Jaenicke and Rudolph, 1986; Buchner, 1996; Jaenicke, 1997). Aggregation is an alternative route to normal folding which competes with correct folding and association. The reason for the aggregation is the formation of incorrect intermolecular interactions (Kiefhaber et al., 1991) which ultimately lead to the formation of heterogeneous aggregates in which the polypeptide chains contained therein are irreversibly lost. It is possible to minimize aggregation in vitro as an undesired side reaction by physico-chemical parameters such as protein concentration, solvent conditions, temperature or ionic strength (Jaenicke and Rudolph, 1989; Kiefhaber et al., 1991; Buchner, 1996; Jaenicke, 1997). In contrast the external conditions for all proteins are constant in vivo. An E. coli cell achieves an apparent folding yield of almost 100% despite the enormous rate of synthesis of ca. 60000 polypeptide chains per minute (Lorimer, 1996). Although misfolding and incorrect assembling of proteins also occurs in vivo (Hurtley and Helenius, 1989; Pelham, 1989; Helenius et al., 1992), this is minimized by several endogenous cell factors. Chaperones or heat shock proteins prevent unspecific aggregation (Buchner et al., 1996) and misfolded proteins or proteins that fold too slowly are degraded (Gottesman and Maurizi, 1992). Mutagenesis studies on heat shock-deficient E. coli strains showed that so-called inclusion bodies occur at elevated growth temperatures (Grangerov et al., 1991). Independently thereof it was shown that the formation of inclusion bodies resulting from the overexpression of recombinant proteins in E. coli can be efficiently suppressed by a simultaneous overexpression of endogenous cell heat shock proteins (Goloubinoff et al., 1989; Dale et al., 1994; Amrein et al., 1995). Protein import into cellular compartments such as mitochondria also depends on heat shock proteins located in the organelles. On the basis of these observations the folding of proteins can be regarded as a spontaneous process which is assisted by folding helper proteins (Horwich et al., 1993; Hendrick and Hartl, 1993; Georgopoulos and Welch, 1993). Hence the precise interplay between these endogenous cell factors reduces incorrect folding processes and promotes the correct folding of polypeptides (Buchner, 1996; Beißinger and Buchner, 1998; Hartl, 1998).

Another important difference between folding in vitro and in vivo is that proteins in the cell are folded vectorially from the N- to the C-terminus (Bergman and Kühl, 1979; Braakman et al., 1991). This process occurs during translation or translocation. The onset of structure formation already occurs while the polypeptide is still at the ribosome or during translocation. This also means that some hydrophobic regions and other potential interaction regions of the polypeptide have to wait for their interaction partner that is still to be synthesized. However, non-appropriate interactions can occur during this synthesis process that can only be reversed under certain conditions and can lead to aggregation reactions. On the other hand disulfide bridges can already be detected in this state in immunoglobulins, serum albumin and haemaglutinin (Bergman & Kühl, 1979; Peters & Davidson, 1982; Braakman et al., 1991). It was shown that folding helper proteins of the Hsp70-chaperone family can already interact with the nascent polypeptide chain during translation on the ribosome (Egers et al., 1997; Frydman et al., 1994; Hansen et al., 1994; Welch et al., 1997). Many other processes such as the import of cytosolically synthesized polypeptide chains into mitochondria are dependent on folding helper proteins (Dekker and Pfanner, 1999). In this connection proteins can only be transported through one or both mitochondrial membranes in a linear unfolded state. In this process molecular chaperones are involved in the unfolding and stabilization of the unfolded state on the cytosolic site of the membrane as well as in the transport and folding in the mitochondria.

In the case of folding in vitro the formation and isomerization of disulfide bridges and the cis/trans-isomerization of prolines are in particular the rate determining folding steps. These folding steps are catalysed by folding assistants in the cell. Protein disulfide isomerases such as PDI or DsbA accelerate redox reactions of cysteines and disulfides in polypeptides depending on the redox conditions (Wunderlich and Glockshuber, 1993; Bardwell, 1997). The acceleration of this folding step reduces the concentration of intermediates during the folding process. This reduces concentration-dependent aggregation and increases the folding yield (Weissman and Kim, 1993; Lillie et al., 1994). Peptidyl-prolyl-cis/isomerases (PPI) catalyse isomerization between the cis and trans form of peptide bonds in front of proline residues in polypeptide chains. In contrast to all other peptide bonds in native proteins, these can be present in their cis configuration (Schmid, 1997).

The E. coli lysate that is frequently used in in vitro translation systems is a natural and optimal system for protein folding. But in contrast to a functional cell, the amount of required chaperones is not automatically adapted to the synthesis output of the translation apparatus. The resulting overloading of the folding machinery in many cases results in the aggregation of the target protein. Various components of the folding machinery can be responsible for this inefficient folding depending on the target protein.

The object of the present invention was to increase the yield of target protein in an in vitro translation system by preventing aggregation of the target protein by providing the required chaperones in an adequate quantity in the in vitro translation system. This should at the same time increase the efficiency of the in vitro translation system.

The object is achieved according to the invention by a method for the expression of target proteins in in vitro translation systems characterized in that folding helper proteins are co-expressed in this system. The co-expressed folding helper proteins are selected from one or several of the following protein classes: Hsp60, Hsp70, Hsp90, Hsp100 protein family, family of the small heat shock proteins and isomerases.

Molecular chaperones are the largest group of folding-assisting proteins and are understood according to the invention as folding helper proteins (Gething and Sambrook, 1992; Hartl, 1996; Buchner, 1996; Beißinger and Buchner, 1998). Due to their overexpression under stress conditions, most molecular chaperones can also be allocated to the group of heat shock proteins (Georgopolous and Welch, 1993; Buchner, 1996), this group is also understood according to the invention as a folding helper protein.

Important folding helper proteins which are encompassed by the present invention are elucidated in more detail in the following. The group of molecular chaperones can be divided on the basis of sequence homologies and molecular masses into five non-related protein classes i.e. the Hsp60, Hsp70, Hsp90, Hsp100 protein families and the family of the small heat shock proteins (Gething and Sambrook, 1992; Hendrick and Hartl, 1993).

Hsp60

The best investigated chaperone overall is GroEL which is a member of the Hsp60 family from *E. coli*. Members of the Hsp60 families are also referred to as chaperonins and are divided into two groups. GroEL and its co-chaperone GroES and their strongly homologous relatives from other bacteria as well as mitochondria and chloroplasts form the group of I chaperonins (Sigler et al., 1998; Fenton and Horwich, 1994). The Hsp60 proteins from the eukaryotic cytosol from Archebacteria together form the group II chaperonins (Gutsche et al., 1999). The Hsp60 proteins in both groups have a similar oligomeric structure. In the case of GroEL and the other group I chaperoning, 14 GroEL subunits associate to form a cylinder composed of two heptamer rings whereas the heptamer ring structure in the group II chaperonins from Archebacteria is usually composed of two different subunits. In contrast members of the group II chaperonins from eukaryotic cytosol such as the CCT complex from yeast are composed of eight different subunits with an exactly defined organisation (Liou and Willison, 1997). Non-native proteins can be intercalated and bound in the central cavity of this cylinder. The co-chaperone GroES also forms a heptameric ring and binds in this form to the poles of the GroEL cylinder. However, this binding of GroES results in a limitation of the substrate binding depending on its size 10–55 kDa; (Ewalt et al., 1997). The substrate binding is regulated by ATP-binding and hydrolysis.

Hsp70

In addition to members of the Hsp60 family, the Hsp70 proteins also bind to the nascent polypeptide chain (Beckman et al., 1990; Welch et al., 1997). There are usually several constitutively expressed and stress-induced members of the Hsp70 families present in prokaryotic as well as in eukaryotic cells (Vickery et al., 1997; Welch et al., 1997). Apart from their involvement in protein folding directly on the ribosome, these proteins are also involved in the translocation of proteins through cell and organelle membranes (Schatz & Doberstein, 1996). It was shown that proteins can only be transported through membranes in an unfolded or partially folded state (Hannavy et al., 1993). During the translocation process in organelles, it is above all the members of the Hsp70 family that are involved in unfolding and stabilization on the cytosolic side as well as in the refolding on the organelle side (Hauke and Schatz, 1997). In all these processes the ATPase activity of Hsp70 is essential for the function of the protein. A characteristic feature of the Hsp70 system is the control of the activity by co-chaperones (Hsp40; DnaJ) in which the equilibrium between substrate binding and release is influenced by specific modulation of the ATPase activity (Bukau and Horwich, 1998).

Hsp90

About 1% of the soluble protein in the eukaryotic cytosol is Hsp90 which is thus one of the most strongly expressed proteins (Welch and Feramisco, 1982). The members of this family mainly act in multimeric complexes where they recognize numerous important signal transduction proteins with similar structures to the native proteins. Binding to Hsp90 and its partner proteins stabilizes these structures and thus facilitates the binding of ligands to the signal proteins. In this manner the substrates can attain their active conformation (Sullivan et al., 1997; Bohen et al., 1995; Buchner, 1999).

Hsp100

Recently the Hsp100 chaperones have been particularly distinguished by their ability in cooperation with the Hsp70 chaperones to dissociate already formed aggregates (Parsell et al., 1994; Goloubinoff et al., 1999; Mogk et al., 1999). Although their main function appears to be the mediation of thermotolerance (Schirmer et al., 1994; Kruger et al., 1994), some members such as ClpA and ClpB together with the protease-subunit ClpP mediate the proteolytic degradation of proteins (Gottesman et al., 1997).

sHsps

The fifth class of chaperones the small heat shock proteins (sHsps) are a very divergent family of heat shock proteins which are found in almost all organisms. The reason for thus naming this family of chaperones is their relatively low monomeric molecular weight of 15–40 kDa. However, sHsps usually exist in the cell as high-oligomeric complexes containing up to 50 subunits which have been observed to have molecular masses of 125 kDa to 2 Mda (Spector et al., 1971; Arrigo et al., 1988; Andreasi-Bassi et al., 1995; Ehrnsperger et al., 1997). Like other chaperones, the sHsps can suppress the aggregation of proteins in vitro (Horwitz, 1992; Jakob et al., 1993; Merck et al., 1993; Jakob and Buchner, 1994, Lee et al., 1995; Ehrnsperger et al., 1997b). In this process sHsps bind up to one substrate molecule per subunit and hence have a higher efficiency than the model chaperone GroEL (Jaenicke and Creighton, 1993; Ganea and Harding, 1995; Lee et al., 1997; Ehrnsperger et al., 1998a). Under stress conditions the binding of non-native protein to sHsps prevents the irreversible aggregation of the proteins. Binding to sHsps holds the proteins in a soluble folding-competent state. After restoring physiological conditions the non-native protein can be detached from the complex with sHsp by ATP-dependent chaperones like Hsp70 and reactivated.

Isomerases

Folding catalysts from the class of peptidyl-prolyl-cis/trans isomerases and members of the disulfide isomerases for example come into consideration as isomerases for the method according to the invention.

Folding helper proteins which function in the same manner or in a similar manner to the folding helper proteins described above are also encompassed by the present invention.

According to the present invention it is preferred that the co-expressed folding helper proteins are members of the Hsp60 protein family. Furthermore co-chaperones are preferably additionally co-expressed. According to the method according to the invention it is particularly preferred that Hsp60 as a folding helper protein and Hsp10 as a co-chaperone are co-expressed. It is particularly preferred that the co-expressed folding helper protein is GroEL. A method is particularly preferred in which GroEL/GroES are co-expressed.

Another preferred variant of the method is that the co-expressed folding helper proteins are members of the Hsp70 protein family. Furthermore co-chaperones are preferably co-expressed in addition. In this variant it is particularly preferred that the co-expressed folding helper protein is a human Hsp70 protein. In particular it is then preferred that Hsp70 as a folding helper protein and Hsp40 as a co-chaperone are co-expressed. According to the method of the invention, Hsp70 from humans and Hdj1 (Hsp40 from humans) are most preferably co-expressed in this variant.

According to the invention the target proteins can be all types of prokaroytic and eukaryotic proteins and also archaeal proteins. The expression of secretory proteins and membrane proteins was previously particularly problematic in in vitro transcription/translation systems especially when folding helper proteins were not present in adequate amounts. Although the successful expression of lipoproteins and membrane proteins has been described in the prior art, it is subject to considerable limitations (Huppa and Ploegh, 1997; Falk et al., 1997). The method according to the invention is particularly suitable for the expression of lipoproteins and membrane proteins and secretory proteins as the target protein since folding helper proteins can be provided by the co-expression in an adequate amount.

An advantage of the method according to the invention is in particular that the increase in the volume yield of the target protein in in vitro transcription/translation systems occurs on a preparative scale.

In vitro translation systems which can be the basis for the present invention and in particular coupled in vitro transcription/translation systems are described in more detail in the following section. At present the most efficient systems are based on $E.$ $coli$, rabbit reticulocyte or wheat-germ lysates (Spirin, 1990; Stiege and Erdman, 1995). They are usually used as batch reactions with a defined reaction volume. $E.$ $coli$-based reactions can be used in a temperature range of 24–38° C. The 30S supernatant of $E.$ $coli$ lysates is usually used for these batch processes which, due to the high content of endogenous mRNA, has to be treated with RNase before using it for in vitro translation (Zubay, 1973). Reactions based on wheat-germ lysates are normally only used in a temperature range of 20–27° C. (Tulin et al., 1995) but have the advantage over $E.$ $coli$ lysates that they can be used directly for the expression of exogenous expression templates due to the low level of endogenous mRNA. Reticulocyte lysates are prepared by direct lysis of anaemic rabbit blood from which the endogenous mRNAs are removed by RNase treatment. These systems are usually used for processes in a temperature range of 30–38° C. (Pelham and Jackson, 1976). However, it should be noted that the working temperature not only has an effect on the translation processes but also that the folding of the target proteins is extremely dependent on the respective working temperature.

Protein synthesis in such batch reactions can only be maintained until the first important components are no longer functional due to degradation, inhibition or lack of energy. The biggest problem in this connection is the energy supply for protein synthesis (Yao et al., 1997, Matveev et al., 1996) which is why only relatively short synthesis times can be achieved in these batch reactions and hence only relatively low yields of target protein (on average 0.1–20 µg/ml) (Mosca et al., 1983).

However, the mRNA required for protein synthesis can also be produced directly in the expression systems. For these so-called coupled transcription/translation systems it is possible to use the endogenous RNA polymerase as well as exogenous phage RNA polymerases to prepare the mRNA in systems based on $E.$ $coli$ lysates (Chen and Zubay, 1983; Köhrer et al., 1996). In contrast exogenous phage RNA polymerases are used in eukaryotic systems (Craig et al., 1992; Baranov and Spirin, 1993). But then of course appropriate DNA templates with corresponding promoter elements are required in such eukaryotic systems.

The problem of short expression times and of the energy supply to the systems was solved with the continuous exchange cell-free translation apparatus (CECF) or continuous flow cell-free translation apparatus (Spirin et al., 1988; Spirin, 1991). The fundamental idea is based on the continuous supply of energy and low-molecular components to the reaction and the continuous removal of low-molecular byproducts. In this connection the reaction is supplied via a semi-permeable membrane from a separate feed compartment.

The in vitro translation system is preferably a coupled in vitro transcription/translation system. The coupled in vitro transcription/translation preferably occurs in a CFCF or CEFC reactor.

Vectors or DNA templates can be used for the co-expression in in vitro transcription/translation systems whose structure corresponds to the expression vectors of the target proteins. In systems based on $E.$ $coli$ lysates it is possible to use promoters for the endogenous $E.$ $coli$ RNA polymerase as well as vectors containing promoters for exogenous viral polymerases. In this connection the vectors should also contain a ribosomal binding site and suitable terminator regions in addition to the promoter regions. In principle it is also possible to use linear DNA expression templates (e.g. PCR product). If circular expression vectors are used which have to be previously amplified in vivo before being used experimentally, they should contain suitable replication starting points and at least one selectable marker. The co-expression time period and the co-expression strength of chaperones can be optimized for the respective substrate proteins (Lottspeich and Zorbas, 1998).

In order to ensure a maximum efficiency of the chaperone machinery during the synthesis reaction, the co-expression should be regulated. An appropriate regulation can be achieved, on the one hand, by the metered addition of the co-expression vectors or, on the other hand, by regulatory sequences in the promoter regions of the vector which can regulate the induction and strength of the expression. IPTG-inducible lac-operator sequences, binding sequences for tetracycline repressors or catabolite-inducible regulatory sequences (e.g. arabinose operator) can be used for such a regulation. However, in this connection separate induction of the target protein expression and of the chaperone co-expression must be taken into consideration.

Hence it is preferable to regulate the co-expression of the folding helper proteins or of the chaperones. In particular it is preferred that the expression of the target proteins can be induced separately from the co-expression of the folding helper proteins or of the co-chaperones.

DNA templates for eukaryotic systems should also be composed of appropriate promoter regions for viral RNA polymerases, the eukaryotic sequences required to initiate translation and suitable terminators. Circular expression vectors that have to be amplified in $E.$ $coli$ for their experimental use, should also contain a replication start sequence for $E.$ $coli$ and at least one selectable marker in $E.$ $coli$. In this case it was also possible to regulate the chaperone co-expression by appropriate regulatory sequences for viral promoters (Lottspeich and Zorbas, 1998).

Since the overloading of the chaperone machinery depends on the respective target protein and the rate of expression of the target protein, the amount of required chaperones depends strongly on the target protein. Hence in individual cases it may be important to optimize the expression rates of both expression templates. Such an optimization can be achieved by varying the amount of expression template used in addition to the direct regulation of expression via promoters. In the case of target proteins that are very susceptible to aggregation it may indeed be necessary to use a large excess of chaperones whereas for other target proteins the strong co-expression of chaperones could even interfere with the expression of the target protein. Depending on the target protein, its functional expression may require the co-expression of single chaperones as well as the co-expression of several chaperones. In this connection it should also be noted that most chaperones only work effectively as complex systems with corresponding co-chaperones. Hence the co-expression of chaperones and appropriate co-chaperones is particularly preferred.

The object according to the invention can also be achieved by adding purified chaperones and co-chaperones in the required amount. However, this process is relatively expensive.

A further subject matter of the present invention is the use of a vector containing a gene coding for a folding helper protein for the method according to the invention. Another subject matter of the present invention is the use of a vector containing a gene coding for a co-chaperone for the method according to the invention.

A special subject matter of the present invention is the use of a vector containing a gene coding for a folding helper protein and additionally containing a promoter region, a ribosomal binding site and a terminator region for the method according to the invention. It is also particularly preferable to use a vector containing a gene coding for a co-chaperone and additionally containing a promoter region, a ribosomal binding site and a terminator region for the method according to the invention.

In the following examples the method according to the invention is carried out in a rapid translation system (RTS system) using mitochondrial citrate synthase as the target protein (porcine heart; EC 4.1.3.7). GFP was used as another target protein. Unexpectedly co-expression of GroEL/ES in the RTS system as well as the addition of GroEL/ES led to an increase in the expression yields on a preparative scale.

FIGURE LEGENDS

FIG. 1: Influence of GroEL/ES on the yield of active, purified CS in the RTS system: CS expression of pIVEX 2.4b without addition of GroEL/ES. CS expression of pIVEX 2.4b, co-expression of GroEL/ES. CS expression of pIVEX 2.4b with addition of 150 nM purified GroEL and 300 nM purified GroES.

Figure 2:
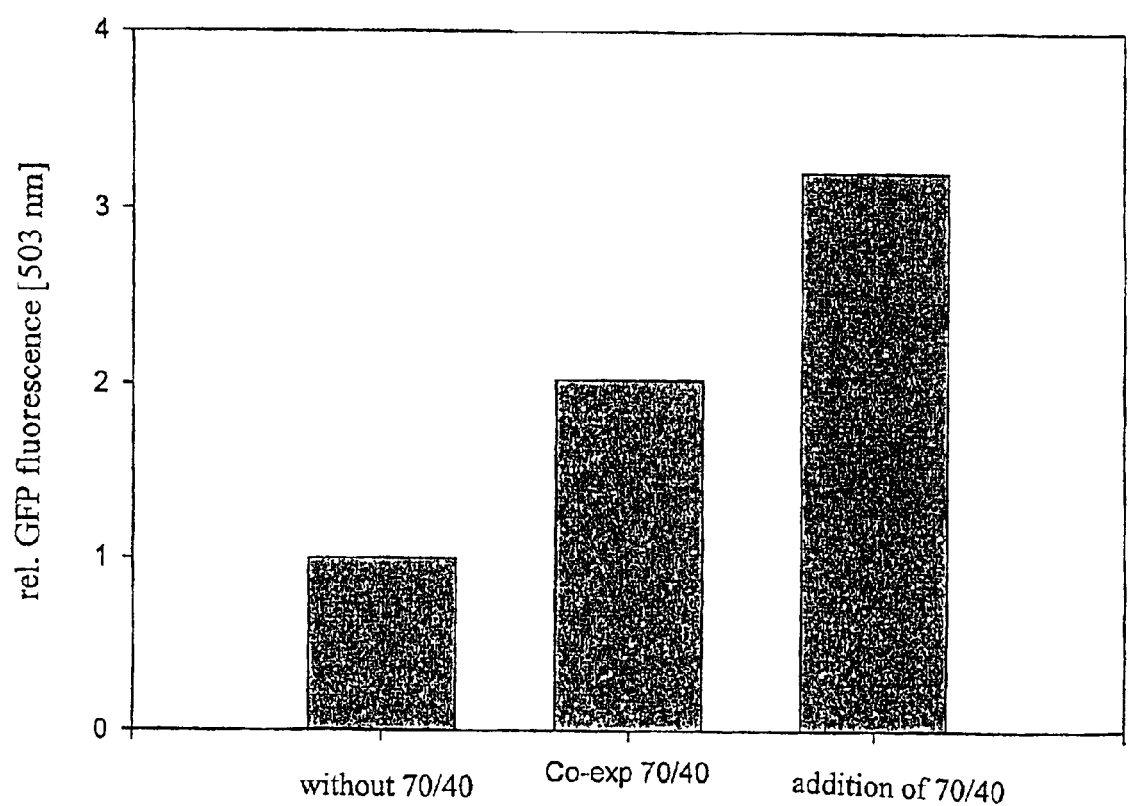

FIG. 2: Influence of Hsp70 and Hsp40 on the yield of GFP in the RTS system: GFP expression without addition of Hsp70 (from humans) and Hdj1 (Hsp40 from humans). GFP expression with co-expression of Hsp70 and Hdj1. GFP expression with addition of 300 nM Hsp70 and 300 nM Hdj1.

BIBLIOGRAPHY

Abravaya K, Myers M P, Murphy S P, Morimoto R I (1992) Genes Dev 6: 1153–1164.
Amrein K E, Takacs B, Stieger M, Molonos J, Flint N A, Burn P (1995) Proc Natl Acad
Arrigo A P, Suhan J P, Welch W J (1988) Mol Cell Biol 8: 5059–5071
Baranov V I, Spirin A S (1993) Methods Enzymol 217: 123–142
Beckman R P, Mizzen L E, Welch W J (1990) Science 248: 850–854
Beissinger M, Buchner J (1998) Biol Chem 379, 245–259
Bergman L, Kühl W M (1979) J Biol Chem 267: 6786–6800
Bohen S P, Kralli A, Yamamoto K R (1995) Science 268: 1303–1304
Braakman I, Hoover-Litty H, Wagner K R, Helenius A (1991) J Cell Biol 114: 401–411
Buchner J (1996) FASEB J 10: 10–19
Buchner J (1999) Trends Biochem Sci 24: 136–141
Bukau B, Horwich A L (1998) Cell 92: 351–66
Chen H Z, Zubay G (1983) Methods Enzymol 101: 674–690
Craig E A (1992) in: The Molecular and Cellular Biology of the Yeast *S. cerevisiae*. Jones E W (Editor) Cold Spring Harbor Laboratory Press, New York, 501–537
Dale G E, Schönfeld H J, Langen, Stieger M (1994) Protein Eng 7: 925–931
Dekker P J T, Pfanner N (1999) in: Molecular Chaperones and folding Catalysts, Bukau B (Editor), Harwood Academic publischers, 235–263
Egers D K, Welch W J, Hansen W J (1997) Mol Biol Cell 8: 1559–1573
Ehrnsperger M, Graber S, Gaestel M, Buchner J (1997) EMBO J 16: 221–229
Ehrnsperger M, Hergersberg C, Wienhues U, Nichtl A, Buchner J (1998) Anal Biochem 259: 218–225
Ewalt K L, Hendrick J P, Houry W A, Hartl F U (1997) Cell 90: 491–500
Falk M M, Buehler L K, Kumar N M, Gilula N B (1997) EMBO J 16:2703–2716
Fenton W A, Kashi Y, Furtak K, Horwich A (1994) Nature 371, 614–619
Frydman J, Nimmersgern, Ohstuka K, Hartl F U (1994) Nature 370: 11–117
Ganea E, Harding J J (1995) Eur J Biochem 231: 181–185
Georgopoulos C, Welch W J (1993) Annu Rev Cell Biol 9: 601–634
Gething M J, Sambrook J F (1992) Nature 355: 33–45
Gottesman S, Maurizi M R, Wickner S (1997) Cell 91: 435–438
Goloubinoff P, Gatenby A A, Lorimer G H (1989) Nature 337: 44–47
Goloubinoff P, Mogk A, Zvi A P, Tomoyasu T, Bukau B (1999) Proc Natl Acad Sci USA 96: 13732–13737
Grangerov A I, Martin E S, Krupenko M A, Kashlev M V, Nikiforov V G (1991) FEBS Lett 291: 22–224
Gutsche I, Essen L O, Baumeister W (1999) J Mol Biol 293: 295–312
Hannavy K, Rospert S, Schatz G (1993) Curr Opin Cell Biol 5: 694–700
Hansen W J, Lingappa V R, Welch W J (1994) J Biol Chem 269: 26610–26613
Hartl F U (1996) Nature 381: 571–579
Hartl F U (1998) Biol Chem 379: 235–240
Hauke V, Schatz G(1997) EMBO J 16: 4560–4567
Hendrick J P, Hartl F U (1993) Annu Rev Biochem 62: 349–384
Horwitz J (1992) Proc Natl Acad Sci 89: 10449–10453
Horwitz J, Bova M P, Ding L L, Haley D A, Stewart P L (1999) Eye 13: 403–408
Huppa J B, Ploegh H L (1997) J Exp Med 186: 393–403
Jaenicke R (1997) in: Molecular Chaperones in the Life Cycle of Proteins. Fink A L, Goto Y, (Editor), Marcel Dekker, New York, 35–70
Jaenicke R, Creighton T E (1993) Curr Biol 3: 234–235
Jaenicke R, Rudolph R (1986) Methods Enzymol 131: 218–250
Jaenicke R, Rudolph R (1989) in: Protein Structure: A Practical Approach. Creighton T E (Editor), IRL Press, Oxford, 191–223
Jakob U, Gaestel M, Engel K, Buchner J (1993) J Biol Chem 268: 1517–1520
Jakob U, Buchner J (1994) Trends Biochem Sci 19: 205–211
Kiefhaber T, Rudolph R, Kohler H H, Buchner J (1991) Bio/Technology 9, 825–829

Köhrer C, Mayer C, Grübner P, Piendl W (1996) Eur J Biochem 236: 234–239

Kruger E, Volker U, Hcker M (1994) J Bacteriol 176: 3360–3367

Lee G J, Pokala N, Vierling E (1995) J Biol Chem 270: 10432–10438

Lee G J, Roseman A M, Saibil H R, Vierling E (1997) EMBO J 16: 659–671

Lillie H, McLaughlin S, Freedman R B, Buchner J (1994) J Biol Chem 269: 14290–14296

Liou A K, Willison K R (1997) EMBO J 16: 4311–4361

Lorimer G H (1996) FASEB J 10: 5–9

Lottspeich F, Zorbas H (1998) Bioanalytik (Hrsg.) Spektrum Verlag, Berlin

Matveev S V, Vnokurov L M, Shaloiko L A, Matveeva E A, Alakhov Y B (1996) Biochim Biophys Acta 1293: 207–212

Mosca J D, Wu J M, Suhadolnik P J (1983) Biochemistry 22: 346–354

Parsell D A, Kowal A S, Singer M A, Lindquist S (1994) Nature 372: 475–478

Pelham H R B, Jackson R J (1976) Eur J Biochem 67: 247–256

Peters T Jr, Davidson L K (1982) J Biol Chem 257: 8847–8853

Schatz G, Doberstein B (1996) Science 271: 1519–1526

Schirmer E C, Lindquist S, Vierling E (1994) Plant Cell 6: 1899–1909

Schmidt M, Bucheler U, Kaluza B, Buchner J (1994) J Biol Chem 269: 27964–27972

Schmid F X (1997) in: Protein Structure: A Practical Approach. Creighton R E (Editor) IRL Press, Oxford, 253–299

Sigler P B, Xu Z, Rye H S, Burston S G, Fenton W A, Horwich A L (1998) Annu Rev Biochem 67: 581–608

Spector A, Li L K, Augusteyn R C, Schneider A, Freund T (1971) Biochem J 124: 337–343

Spirin A S, Baranov V I, Ryabova L A, Ovodov S Y, Alakhov Y B (1988) Science 242: 1162–1164

Spirin A S (1990) in: The Ribosome: Structure, Funktion and Evolution. Hill E H, Dahlberg A Garrot R A, Moore P B, Schlessinger D, Warrner J R, Washington D.C. (Editors) American Society for Microbiology, 56–70

Spirin A S (1991) in: Frontiers in Bioprocessing II. Todd P, Skidar S K, Bier M, Washington D.C. (Editors) American Chemical Society, 31–43

Stiege W, Erdman V A (1995) J Biotechnol 1995 41: 81–90

Sullivan W, Stensgard B, Caucutt G, Bartha B, McMahon N, Alnemri E S, Litwack G, Toft D (1997) J Biol Chem 272: 8007–8012

Tulin E E, Ken-Ichi T, Shin-Ichiro E (1995) Biotechnol Bioeng 45: 511–516

Vickery L E, Silberg J J, Ta D T (1997) Protein Sci 6: 1047–1056

Welch W J, Feramisco J R (1982) J Biol Chem 257: 14949–14959

Welch W J, Eggers D K, Hansen W J, Nagata H (1997) in: Molecular Chaperones in Life Cycle of Proteins. Fink A L, Goto Y (Editors) Marcel Dekker, New York, 71–93

Weissman J S, Kim P S (1993) Nature 365, 185–188

Wunderlich M, Glockshuber R (1993) Prot Sci 2: 717–726

Yao S L, Shen X C, Suzuki E (1997) J Ferment Bioeng 84: 7–13

Zubay G (1973) Annu Rev Genet 7: 267–287

EXAMPLE 1

A pIVEX 2.4b vector (Roche, Molecular Biochemicals) containing the citrate synthase gene was used for expression in the RTS system which expresses the citrate synthase gene with a His-tag fused to the N-terminus. The reactions were carried out for 24 h at 27° C., 140 rpm using RTSmini kits of lot No. 85869220 (Roche, Molecular Biochemicals).

The aggregation of the expressed citrate synthase was suppressed by, on the one hand, co-expressing GroEL/ES and, on the other hand, by adding purified GroEL/ES to the RTS reactions.

8 μg pIVEX 2.4b and 8 μg of the GroEL/ES-expressing plasmid was used in each case. The GroEL/ES-expressing plasmid corresponds to a modified pET vector (Novagen, Milwaukee, USA) which expresses the GroEL/ES operon under the control of a T7 promoter (Ishii Yasuhawa et al., 1995). The expression of the 3 proteins was checked with SDS-PAGE and immunoblot. All proteins are expressed in approximately equal amounts.

The GroEL/ES used for the addition, was purified as described in Schmidt et al., (1994). 150 nM GroEL and 300 nM GroES were added to the RTS system.

After completion of the RTS reaction, the reaction mixtures were centrifuged for 10 min at 14000 g and 4° C. in order to separate aggregates from the soluble components. The soluble fraction was diluted 1:10 with Ni-NTA equilibration buffer (100 mM $Na_2HPO_4$, 300 mM NaCl, pH 7.4) and loaded at a continuous flow rate of 0.5 ml/min onto a 1 ml Ni-NTA Superflow column (Quiagen). The column was firstly washed with 5 ml equilibration buffer and subsequently with 5 ml washing buffer (100 mM $Na_2HPO_4$, 300 mM NaCl, 30 mM imidazole, pH 6.8). The citrate synthase was then eluted from the column with 3 ml elution buffer (100 mM $Na_2HPO_4$, 300 mM NaCl, 300 mM imidazole, pH 7.5).

Co-enzyme A that is formed as a byproduct of the condensation of oxaloacetate stoichiometrically reduces Ellman's reagent (DNTB) which is associated with an increase in the absorption at 412 nm. Correctly folded active citrate synthase can be detected with this reaction. For the activity determination 50 μl of the purified citrate synthase (elution fraction), 900 μl TE buffer (50 mM Tris/HCl, 2 mM EDTA, pH 8.0), 10 μl oxaloacetate (10 mM in 50 mM Tris), 10 ml DTNB (in TE buffer) and 30 μl acetyl-CoA (in TE buffer) were mixed and incubated at 25° C. The change in absorbance was measured continuously over a period of 5 min and the change in absorbance per minute was determined. The change in absorbance of purified citrate synthase was averaged in each case from three different RTS reactions. The averaged absorbance change in the RTS reactions without GroEL/ES co-expression was normalized to 1.

RESULT

As shown in FIG. 1 both approaches lead to high yields of active purified mitochondrial citrate synthase. Surprisingly the co-expression of the GroEL/ES system worked just as well as the direct addition of purified GroEL and GroES. The yield of active purified target protein was increased 5-fold by the co-expression of GroEL/ES.

EXAMPLE 2

GFP was used as a model substrate to examine the effects of Hsp70 chaperones on expression in the RTS system,. The reactions were carried out for 24 h at 27° C., 140 rpm using the RTSmini kit lot No. 85869220 (Roche, catalogue). In order to ensure that GFP was oxidized during the reaction, only half amounts were used. In each case 5 μg of the GFP control plasmid contained in the RTSmini kit was used.

In order to examine the effects of Hsp70 on the expression yield in the system, human Hsp70 and Hsp40 were co-expressed, and on the other hand, purified Hsp70 and Hsp40 were added to the RTS reactions. 8 μg of the Hsp70 and Hsp40 expression plasmids were used in each case. The Hsp70-expressing plasmid corresponds to a pET11a vector (Novagen, Milwaukee, USA), the Hsp40 (Hdj1) expressing plasmid corresponds to a pET21d vector (Novagen, Milwaukee, USA), both genes were expressed under the control of a T7 promoter. 300 nM Hsp70 and 300 nM Hdj1 were added to the RTS system (Abravaya et al., 1992).

After completion of the RTS reaction, the reaction mixtures were centrifuged for 10 min at 14000 g and 4° C. to separate the aggregates from the soluble components. The fluorescence emission of the soluble fractions was measured at 430–580 nm at an excitation of 395 nm. The relative fluorescence at 503 nm of the mixture without addition or co-expression of chaperones was normalized to 1 and compared to the fluorescence of the mixtures containing chaperones. In order to exclude the effects of the subsequent oxidation of GFP, the samples were measured again after 24 hours but no differences were observed.

RESULT

As shown in FIG. 2, both approaches lead to high yields of active GFP. Surprisingly the addition as well as the co-expression of Hsp70 chaperones worked. The yield of active target protein was doubled by the co-expression of Hsp70 and Hsp40. Direct addition led to an increase of the yield by more than 3-fold.

I claim:

1. A method for the expression of a target protein in an in vitro translation system, said method comprising preparing a reaction mixture comprising a lysate, a gene coding for the target protein and a gene coding for a folding helper protein, co-expressing the target and helper proteins, and separating the target protein from the mixture, wherein the co-expression is regulated by metered addition of the gene coding for the folding helper protein or by providing a vector comprising the gene coding for the folding helper protein and a regulatory seciuence for regulating induction and strength of the expression.

2. The method of claim 1, wherein the co-expressed folding helper protein is selected from the group consisting of Hsp60 proteins, Hsp70 proteins, Hsp90 proteins, Hsp100 proteins, small heat shock proteins, and isomerases.

3. The method of claim 1, wherein the co-expressed folding helper protein is an Hsp60 protein.

4. The method of claim 1, wherein the reaction mixture further comprises a gene coding for a co-chaperone and the co-chaperone is additionally co-expressed.

5. The method of claim 4, wherein the co-chaperone is an Hsp10 protein.

6. The method of claim 3, wherein the co-expressed folding helper protein is GroEL.

7. The method of claim 4, wherein the co-chaperone is GroES.

8. The method of claim 1, wherein the co-expressed folding helper protein is a Hsp70 protein.

9. The method of claim 8, wherein the reaction mixture further comprises a gene coding for a co-chaperone and the co-chaperone is additionally co-expressed.

10. The method of claim 8, wherein the Hsp70 protein is a human Hsp70 protein.

11. The method of claim 9, wherein Hsp40 is co-expressed as a co-chaperone.

12. The method of claim 8, wherein human Hsp40 is also co-expressed.

13. The method of claim 1, wherein the in vitro translation system is a coupled in vitro transcription/translation system.

14. The method of claim 13, wherein the coupled in vitro transcription/translation system is a continuous flow cell-free system or a continuous exchange cell-free system.

15. The method of claim 1 wherein the target protein is citrate synthase.

16. The method of claim 15 wherein the helper protein is GroEL.

17. The method of claim 1 wherein the target protein is green fluorescent protein (GFP).

18. The method of claim 17 wherein the helper protein is an Hsp70 protein.

* * * * *